United States Patent [19]
Birch

[11] Patent Number: 5,693,654
[45] Date of Patent: Dec. 2, 1997

[54] MEDICAMENTS FOR TREATING INTRAOCULAR PRESSURE

[75] Inventor: Phillip John Birch, Greenford, Great Britain

[73] Assignee: Glaxo Group Limited, London, England

[21] Appl. No.: 373,272

[22] PCT Filed: Jul. 30, 1993

[86] PCT No.: PCT/EP93/02041

§ 371 Date: Feb. 6, 1995

§ 102(e) Date: Feb. 6, 1995

[87] PCT Pub. No.: WO94/03162

PCT Pub. Date: Feb. 17, 1994

[30] Foreign Application Priority Data

Jul. 31, 1992 [GB] United Kingdom ............... 9216380

[51] Int. Cl.⁶ .................. A61K 31/445; A61K 31/40
[52] U.S. Cl. .................... 514/323; 514/414; 514/913
[58] Field of Search .................................. 514/323, 414, 514/913

[56] References Cited

PUBLICATIONS

Barnett et al., *Exp. Eye Res.*, 57, 2, Aug. 1993, 209–216.
Tobin et al., *J. Neurochem.*, 53, 3, Sep. 1989, 686–691.
Meyer–Bothling et al., *Invest. Ophthalmol. Vis. Sci.*, 34, 10, Sep. 1993, 3035–3042.
Zschauer et al., *Am. J. Physiol.*, 261, 6Pt2, Dec. 1991, H1819–H1827.
Osborne et al., *Neurochem. Int.*, 19, 4, 1991, 407–411.
Osborne et al., *Neurol. Neurobiol.*, 49, 1989, 159–175.
Mangel et al., *Vis. Neurosci.*, 8, 3, Mar. 1992, 213–218.

*Primary Examiner*—Zohreh Fay
*Attorney, Agent, or Firm*—Bacon & Thomas

[57] ABSTRACT

This invention relates to a new medical use for compounds having selective agonist activity at $5\text{-HT}_1$-like receptors and to pharmaceutical compositions containing them. In particular it relates to a new medical use of 3-[2-(dimethylamino)ethyl]-N-methyl-1H-indole-5-methanesulphonamide and physiologically acceptable salts and solvates thereof for the treatment or prevention of elevated intraocular pressure, in particular glaucoma.

18 Claims, No Drawings

MEDICAMENTS FOR TREATING INTRAOCULAR PRESSURE

This invention relates to a new medical use for compounds having selective agonist activity at $5\text{-}HT_1$-like receptors and to pharmaceutical compositions containing them. In particular it relates to a new medical use of 3-[2-(dimethylamino)ethyl]-N-methyl-1H-indole-5-methanesulphonamide and physiologically acceptable salts and solvates thereof.

$5\text{-}HT_1$-like receptors are located, for example, in the dog saphenous vein and the $5\text{-}HT_1$-like receptor agonists with which the present invention is concerned contract the dog saphenous vein. Such compounds may therefore be identified by their contractile effect on the dog isolated saphenous vein strip as described, for example, by Apperley et al., Br. J. Pharmacol, 68, 215–224 (1980). Compounds which are selective $5\text{-}HT_1$-like receptor agonists have also been found to selectively constrict the carotid arterial bed of the anaesthetised dog.

A variety of compounds which selectively constrict the dog isolated saphenous vein strip and which constrict the carotid arterial bed of the anaesthetised dog have been described in the art. These include indole derivatives such as those disclosed inter alia in published British Patent Specifications Nos. 2982175, 2081717, 2083463, 2124210, 2150932, 2162522, 2168347, 2168973, 2185020, 2186874, 2191488, 2208646, published European Patent Specifications Nos. 147107, 237678, 242939, 244085, 225726, 254433, 303506, 313397, 354777, 382570, 464558, 506363, 506369, 450238, 451022, 451008, 478954, 438230, 494774, 497512, 501568 and published International patent application Nos. WO92/11013, WO92/11014, WO92/06973, WO93/00086, WO92/13856, WO93/00094, WO91/18897 and WO93/00333.

The compounds disclosed in the aforementioned patent specifications have been described as useful in treating and/or preventing pain resulting from dilatation of the cranial vasculature, in particular migraine and related disorders such as cluster headache.

We now find that such compounds are also of use in the treatment of certain ocular disorders.

Glaucoma is a serious progressive clinical condition caused by an imbalance in the flow of intraocular fluids, leading to elevated intraocular pressure, optic nerve degeneration and eventual blindness. Current medical therapy for glaucoma is dominated by pharmacological agents which act by reducing the flow of fluid into the ocular chamber, for example beta blockers, and the side-effect profiles of such drugs severely limit their clinical use. Thus, there is a real need to develop new medicines in this area of ophthalmic disease.

Surprisingly, compounds which are selective $5\text{-}HT_1$-like receptor agonists reduce elevated intraocular pressure and are effective in the treatment of glaucoma.

According to one aspect of the invention we therefore provide a selective $5\text{-}HT_1$-like receptor agonist or a physiologically acceptable salt or solvate thereof for use in the treatment or prevention of elevated intraocular pressure, in particular glaucoma e.g. high tension glaucoma and low tension glaucoma.

Particularly preferred compounds for use in the treatment or prevention of elevated intraocular pressure are 3-[2-(dimethylamino)ethyl]-N-methyl-1H-indole-5-methanesulphonamide and N-methyl-3-(1-methyl-4-piperidinyl)-1H-indole-5-ethanesulphonamide, especially 3-[2-(dimethylamino)ethyl]-N-methyl-1H-indole-5-methanesulphonamide.

3-[2-(Dimethylamino)ethyl]-N-methyl-1H-indole-5-methanesulphonamide, which may be represented by the formula (I)

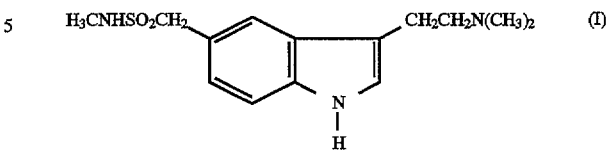

and its physiologically acceptable salts and solvates are disclosed in GB 2162522. Numerous clinical studies have demonstrated the effectiveness of the compound of formula (I) (generic name sumatriptan) in migraineurs.

Thus, a particularly preferred aspect the present invention provides the compound of formula (I) or a physiologically acceptable salt or solvate thereof for use in the treatment or prevention of elevated intraocular pressure.

In an alternative or further aspect, the invention provides a method of treatment of a mammal, including man, suffering from or susceptible to elevated intraocular pressure which comprises administering an effective amount of a selective $5\text{-}HT_1$-like receptor agonist or a physiologically acceptable salt or solvate thereof.

It will be appreciated that whilst selective $5\text{-}HT_1$-like receptor agonists will primarily be of use in the alleviation of established symptoms, prophylaxis is not excluded.

In a further aspect, the invention provides the use of a selective $5\text{-}HT_1$-like receptor agonist or a physiologically acceptable salt or solvate thereof in the manufacture of a medicament for the treatment or prevention of elevated intraocular pressure.

A further aspect of the invention provides pharmaceutical compositions for the treatment or prevention of elevated intraocular pressure comprising as active ingredient a selective $5\text{-}HT_1$-like receptor agonist or a physiologically acceptable salt or solvate thereof.

In a preferred aspect the invention provides a pharmaceutical composition for topical administration to the eye which comprises as active ingredient a selective $5\text{-}HT_1$-like receptor agonist or a physiologically acceptable salt or solvate thereof, together with a pharmaceutically acceptable carrier or excipient.

Suitable physiologically acceptable salts of selective $5\text{-}HT_1$-like receptor agonists include acid addition salts formed with organic or inorganic acids for example hydrochlorides, hydrobromides, sulphates, nitrates, phosphates, formates, mesylates, citrates, benzoates, fumarates, maleates and succinates.

In a particularly preferred embodiment of the present invention, the selective $5\text{-}HT_1$-like receptor agonist employed is the compound of formula (I) in the form of the succinate (1:1) salt or the hemisulphate (2:1) salt.

The compound for use according to the invention may be administered as the raw chemical comprising the active ingredient in an amount of from 0.1 mg to 300 mg.

Conveniently, the compound for use according to the invention may be formulated in conventional manner using one or more pharmaceutically acceptable carriers or excipients. Thus, the compound for use according to the invention may for example be formulated for oral, sub-lingual, buccal, parenteral, rectal or intranasal administration or in a form suitable for administration by inhalation or insufflation (either through the mouth or nose) or in a form suitable for topical administration, preferably for local application in the eye.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compound for use according to the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multi-dose containers, optionally with an added preservative.

The compositions for parenteral administration may take such forms as suspensions, solutions or emulsions in oily or aqueous vehicles, and may contain formulatory agents such as suspending, stabilising and/or dispersing agents. Alternatively, the active ingredient may be in dry form such as a powder, crystalline or freeze-dried solid for constitution with a suitable vehicle, e.g. sterile pyrogen-free water or isotonic saline before use. They may be presented, for example, in sterile ampoules or vials.

The compound for use according to the invention may also be formulated in rectal compositions such as suppositories or retention enemas, e.g. containing conventional suppository bases such as cocoa butter or other glyceride.

Tablets for sub-lingual administration may be formulated in a conventional manner.

For intranasal administration the compound for use according to the invention may be used, for example, as a liquid in the form of, for example, a solution, suspension or emulsion, presented in the form of a spray or drops, or as a powder. Preferably the preparation for intranasal administration is delivered in the form of a spray or aerosol from an insufflator or from a pressurised pack or nebuliser with the use of a suitable propellant.

For administration by inhalation the compound for use according to the invention is conveniently delivered in the form of an aerosol spray presentation from pressurised packs or a nebuliser, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For topical administration the pharmaceutical compositions may be liquids, for example solutions, suspensions or emulsions presented in the form of creams, gels or drops suitable for local application to the eye.

It will be appreciated that the precise dose administered will depend on the age and condition of the patient and the frequency and route of administration and will be at the ultimate discretion of the attendant physician. The compound may be administered in single or divided doses and may be administered one or more times, for example 1 to 4 times per day.

A proposed dose of the active ingredient for use according to the invention for oral, sub-lingual, parenteral, buccal, rectal, intranasal or topical administration to man (of approximately 70 kg bodyweight) for the treatment of glaucoma may be 0.1 to 300 mg of the active ingredient per unit dose which could be administered, for example, 1 to 4 times per day.

For oral administration a unit dose will preferably contain from 2 to 200 mg, more preferably 20 to 100 mg of the active ingredient. Dosages of the compound for use according to the invention for rectal or sub-lingual administration are similar to those for oral administration. A unit dose for parenteral administration will preferably contain 0.1 to 15 mg, more preferably 0.2 to 10 mg of the active ingredient. For intranasal administration a unit dose may contain 1 to 100 mg, preferably 2 to 50 mg of the active ingredient.

Aerosol formulations are preferably arranged so that each metered dose or 'puff' delivered from a pressurised aerosol contains 0.2 mg to 2 mg of a compound for use according to the invention. Capsules and cartridges suitable for use in an insufflator or an inhaler may contain 0.2 mg to 20 mg of a compound of the invention. The overall daily dose by inhalation with an aerosol will be within the range 1 mg to 100 mg. Administration may be several times daily, for example from 2 to 8 times, giving for example 1,2 or 3 doses each time.

I claim:

1. A method of treatment of a mammal, including man, suffering from or susceptible to elevated intraocular pressure which comprises administering to said mammal an effective amount of a selective 5-$HT_1$ receptor agonist or a physiologically acceptable solvent thereof.

2. The method of claim 1 which is for the treatment or prevention of glaucoma.

3. The method of treatment according to claim 1 wherein the selective 5-$HT_1$ receptor agonist is 3-[2-(dimethylamino)ethyl]-N-methyl-1H-indole-5-methanesulphonamide or N-methyl-3-(1-methyl-4-piperidinyl)-1H-indole-5-ethanesulphonamide.

4. The method of treatment according to claim 2 wherein the selective 5-$HT_1$ receptor agonist is 3-[2-(dimethylamino)ethyl]-N-methyl-1H-indole-5-methanesulphonamide or N-methyl-3-(1-methyl-4-piperidinyl)-1H-indole-5-ethanesulphonamide.

5. The method of treatment according to claim 3 wherein the selective 5-$HT_1$ receptor agonist is 3-[2-(dimethylamino)ethyl]-N-methyl-1H-indole-5-methanesulphonamide.

6. The method of treatment according to claim 4 wherein the selective 5-$HT_1$ receptor agonist is 3-[2-(dimethylamino)ethyl]-N-methyl-1H-indole-5-methanesulphonamide.

7. The method of treatment according to claim 1 wherein the medicament is adapted for oral administration.

8. The method of treatment according to claim 2 wherein the medicament is adapted for oral administration.

9. The method of treatment according to claim 3 wherein the medicament is adapted for oral administration.

10. The method of treatment according to claim 4 wherein the medicament is adapted for oral administration.

11. The method of treatment according to claim 1 wherein the medicament is adapted for topical administration to the eye.

12. The method of treatment according to claim 2 wherein the medicament is adapted for topical administration to the eye.

13. The method of treatment according to claim 3 wherein the medicament is adapted for topical administration to the eye.

14. The method of treatment according to claim 4 wherein the medicament is adapted for topical administration to the eye.

15. The method of treatment according to claim 1 wherein the medicament contains a unit dose of 0.1 to 300 mg of a selective 5-$HT_1$ receptor agonist or a physiologically acceptable salt or solvate thereof.

16. The method of treatment according to claim 2 wherein the medicament contains a unit dose of 0.1 to 300 mg of a selective 5-$HT_1$ receptor agonist or a physiologically acceptable salt or solvate thereof.

17. The method of treatment according to claim 3 wherein the medicament contains a unit dose of 0.1 to 300 mg of a selective 5-$HT_1$ receptor agonist or a physiologically acceptable salt or solvate thereof.

18. The method of treatment according to claim 4 wherein the medicament contains a unit dose of 0.1 to 300 mg of a selective 5-$HT_1$ receptor agonist or a physiologically acceptable salt or solvate thereof.

* * * * *